United States Patent
Lin et al.

(10) Patent No.: US 6,847,294 B1
(45) Date of Patent: Jan. 25, 2005

(54) RADIO MEDICAL MONITORING METHOD AND RADIO MEDICAL MONITORING SYSTEM

(76) Inventors: Wei-Kang Lin, 6F, 14, Lane 65, Tung-Pei Street, Taipei (TW); Shih-Yu Tsou, 12F-4, 91, Hsin-I Road Section 2, Taipei (TW); Chih-I Lin, 14292 Spring Vista La., Chino Hills, CA (US) 91709; Shengfu Lin, 3F, 7, Lane 110, Chien-Kang Street, Taipei (TW)

( * ) Notice: Subject to any disclaimer, the term of this patent is extended or adjusted under 35 U.S.C. 154(b) by 1022 days.

(21) Appl. No.: 09/633,879

(22) Filed: Aug. 7, 2000

(30) Foreign Application Priority Data

Dec. 16, 1999 (TW) ........................................ 88122176 A

(51) Int. Cl.$^7$ ............................................. G08B 23/00
(52) U.S. Cl. ................... 340/539.12; 340/573.1
(58) Field of Search .................... 340/539.12, 573.1; 607/32, 60; 600/485; 128/903, 904; 702/19; 706/924

(56) References Cited

U.S. PATENT DOCUMENTS

| | | | |
|---|---|---|---|
| 5,416,695 A | | 5/1995 | Stutman et al. ............. 364/413 |
| 5,564,429 A | | 10/1996 | Bornn et al. ................ 128/696 |
| 5,576,952 A | * | 11/1996 | Stutman et al. ............. 600/300 |
| 5,752,976 A | * | 5/1998 | Duffin et al. ................ 607/32 |
| 5,907,291 A | * | 5/1999 | Chen et al. ............ 340/870.16 |
| 5,935,060 A | | 8/1999 | Iliff ............................ 600/300 |
| 5,959,529 A | * | 9/1999 | Kail, IV ................ 340/539.12 |
| 6,080,106 A | * | 6/2000 | Lloyd et al. ................ 600/300 |
| 6,364,834 B1 | * | 4/2002 | Reuss et al. ................ 600/300 |

FOREIGN PATENT DOCUMENTS

| | | |
|---|---|---|
| EP | 0655218 A1 | 5/1992 |
| JP | 3-158961 | 7/1991 |
| JP | 5-316206 | 11/1993 |
| JP | 7-219780 | 8/1995 |
| JP | 9-251714 | 9/1997 |
| JP | 10-326192 | 12/1998 |
| WO | WO 94/24929 | 11/1994 |
| WO | WO 96/25877 | 8/1996 |
| WO | WO 00/15103 | 3/2000 |

* cited by examiner

*Primary Examiner*—Toan N. Pham
(74) *Attorney, Agent, or Firm*—Bacon & Thomas PLLC

(57) ABSTRACT

A radio medical monitoring system is disclosed, which comprises a modem; a central processing unit (CPU) connected with the modem for digital data transmission therewith; a read-only-memory (ROM) connected with the CPU; a memory connected with the CPU; one or a plurality of digital medical sensors connected with the CPU for transmitting signals from a subject under examination to the CPU; a radio transceiver connected with the modem for receiving/transmitting radio waves and performing an analog signal transmission with the modem. The monitoring system of the present invention has Group ID (GID) and Sort ID functions, and automatically replies according to the order of the Sort ID after identifying the Group ID and confirming that it is necessary to reply. The present invention also discloses a radio medical monitoring method.

11 Claims, 4 Drawing Sheets

RADIO MEDICAL MONITORING METHOD AND RADIO MEDICAL MONITORING SYSTEM

BACKGROUND

The present invention relates to a radio medical monitoring method and a radio medical monitoring system, particularly to a radio medical monitoring method having automatic and sequential reply functions and a radio medical monitoring system having automatic and sequential reply functions.

According to the current practice in the medical profession, a medical staff measures and records different, medical parameters of a patient, such as the body temperature, the heart beat, the blood pressure, the oxygen level in blood, etc., for a patient therefor causing a serious waste in manpower. Presently, the medical profession has adopted a wide varieties of electronic medical sensors to measure different medical parameters. Therefore, theoretically it is possible to perform a remote monitoring on a patient by networking. Regardless of using a wired or wireless remote monitoring, however, the current reply systems are all one-to-one single call and can not use a group call of one to plural or a total call to automatically and sequentially reply patients' data to a monitoring system.

SUMMARY OF THE INVENTION

One objective of the present invention is to provide a radio medical monitoring method.

Another objective of the present invention is to provide a radio medical monitoring system.

A further objective of the present invention is to provide a radio medical monitoring method capable of performing automatic and sequential replies.

A still further objective of the present invention is to provide a radio medical monitoring system capable of performing automatic and sequential replies.

A radio medical monitoring system constructed according to the present invention comprises:

a modem;

a central processing unit (CPU) connected with said modem for digital data transmission therewith;

a read-only-memory (ROM) connected with said central processing unit;

a memory connected with said central processing unit;

one or a plurality of digital medical sensors connected with said central processing unit for transmitting signals from a subject under examination to said central processing unit;

a radio transceiver connected with said modem for receiving/transmitting radio waves and performing an analog signal transmission with said modem;

characterized in that said monitoring system has Group ID (GID) and Sort ID functions, and automatically replies according to the order of the Sort ID after identifying the Group ID and confirming that it is necessary to reply.

DETAILED DESCRIPTION OF THE INVENTION

Figure 1:
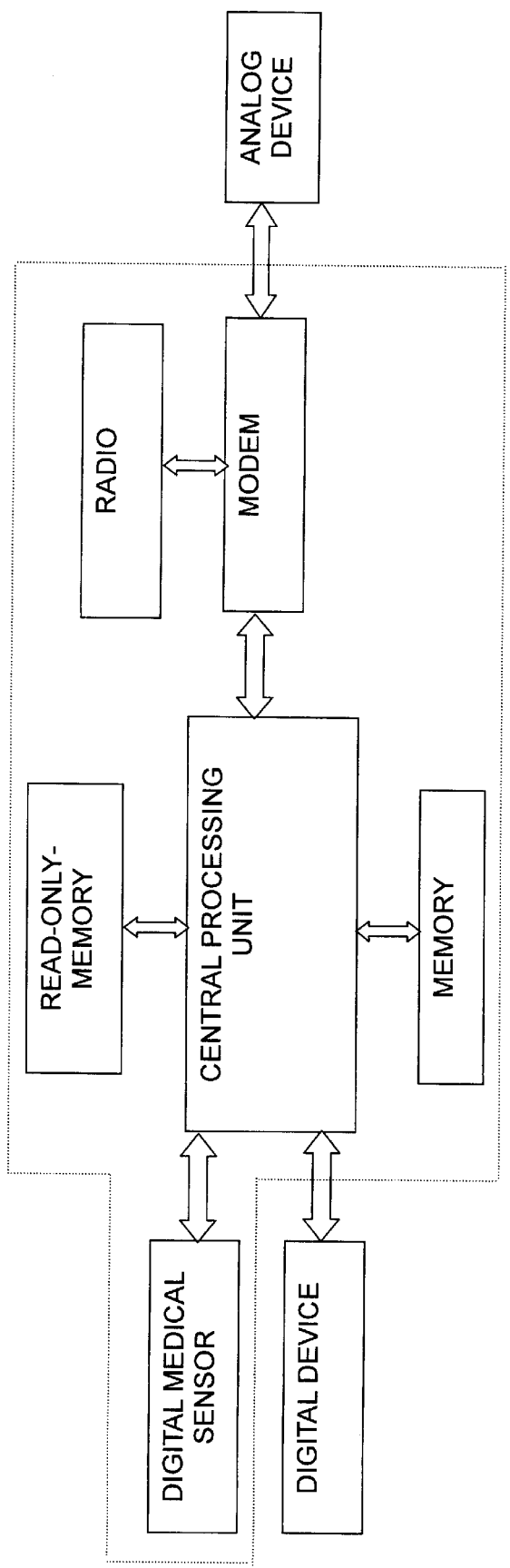
FIG. 1 is a schematic block diagram of a radio medical monitoring system according to the present invention.

The invented radio medical monitoring system comprises:

a modem;

a central processing unit (CPU) connected with said modem for digital data transmission therewith;

a read-only-memory (ROM) connected with said central processing unit;

a memory connected with said central processing unit;

one or a plurality of digital medical sensors connected with said central processing unit for transmitting signals from a subject under examination to said central processing unit;

a radio transceiver connected with said modem for receiving/transmitting radio waves and performing an analog signal transmission with said modem;

characterized in that said monitoring system has Group ID (GID) and Sort ID functions, and automatically replies according to the order of the Sort ID after identifying the Group ID and confirming that it is necessary to reply.

Said digital medical sensor can be an arbitrary digital medical sensor, or an analog electronic medical sensor plus an analog/digital converter (ADC) or a similar device capable of outputting digital signals, and preferably is a digital human parameter sensor, a medical chemical sensor, a biochemical sensor, or a bio-sensor, such as a digital thermometer, a digital manometer, a digital heartbeat meter, a digital sensor for oxygen in blood, that are available on the market.

The above-mentioned modem can be an arbitrary conventional modem integrated circuit (IC) or a commercially available modem, or a re-assembled or modified one thereof.

Said CPU can be an arbitrary conventional CPU, or a chipset or similar component having identical functions.

Said ROM can be an erasable programmable read only memory (EPROM), an electrically erasable programmable read only memory (EEPROM), a flash memory, or a similar IC or device, for storing system programs, constant parameters (e.g., system codes, i.e. SID) and/or main programs, etc.

Said memory can be an ordinary memory, such as a static random access memory (SRAM), a flash memory; or an external memory, such as a floppy disk drive (FDD), a hard disk drive (HDD), a compact disk ROM (CD-ROM), etc., for storing variable programs, variable parameters (such as a Group ID, a Sort ID), etc.

Said radio transceiver can be an IC with radio transceiving functions or a commercial radio transceiver, or a re-assembled or modified one thereof.

The connections between said modem and said CPU, between said CPU and said ROM, between said CPU and said memory, and between said modem and said radio transceiver can all be done by an arbitrarily conventional connection method, such as a bus connection. Of course, a single chip, such as one consisted of a ROM and a CPU, can also be used.

Said modem can be externally connected with an arbitrary analog device, such as a speaker, a microphone, etc.

Said CPU can be externally connected with an arbitrary digital device, such as a scanner, a computer, etc.

Said Group ID (GID) designates a portion of patients to form a patient group among the whole patients. Said patient group has a particular group ID. Of course, the whole patients can comprise one or more patient groups, i.e. the monitoring method according to the present invention comprises one or more Group IDs. If two bytes are used as a Group ID, there can be up to 65536 Group IDs. A Group ID per se can also include a debugging code. For example, when two bits are used as a debugging code, the Group ID formed of two bytes can have up to 16384 Group IDs. Of course, the total number of patients can use up all the Group IDs or only use a portion of the Group IDs—depending on the number of the patient groups. Furthermore, any patient can be arbitrarily chosen to join one or more patient groups or not to join any patient group. Different patient groups may own completely identical patients, partially identical patients or completely different patients. Some patient groups may even be a subset of another patient group.

Said Sort IDs designate patients of the same Group ID so that patients have an order in said Group ID, and thus replies can be carried out according to said order of Sort IDs when said Group ID is received and replies are needed. The Sort IDs of patients within one Group ID can be discontinuous, and preferably are continuous and different from one another.

Said monitoring system can use a System ID (SID) and a code ID (CID) of a patient for a full call (using SID) or a single call (using CID). Of course, a full call can also be viewed as one type of group calls (using GID). The term "full call" used in the present invention designates a call to all patients; whereas the term "single call" designates a call to a single patient.

Figure 2:
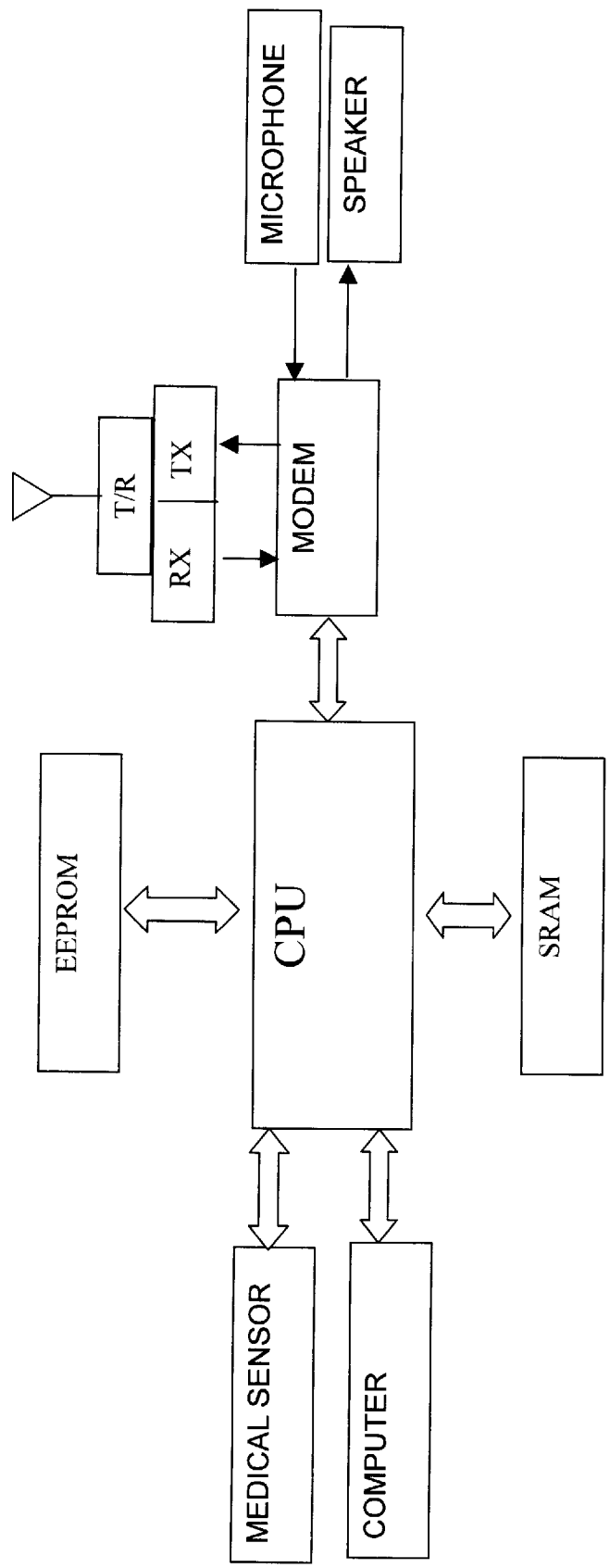
FIG. 2 is a block diagram of a preferred embodiment of the radio medical monitoring system according to the present invention.

FIG. 1 is a schematic block diagram of a monitoring system according to the present invention. The components within the dotted-line frame are essential components. Said CID and said GID are stored in the memory. FIG. 2 is the block diagram of a preferred embodiment of a monitoring system of the present invention wherein said ROM is EEPROM; said memory uses a SRAM; said analog device uses a speaker and a microphone; said digital device is a personal computer (PC); and said CID and said GID are all stored in the SRAM.

The invented radio medical monitoring method comprises:

(1) after receiving a signal by a signal receiving end, identifying a System ID in said signal;

(2) after confirming said System ID, identifying a Group ID in said signal;

(3) after confirming said Group ID, identifying a Reply ID in said signal;

(4) after confirming that a reply is needed, automatically and sequentially replying examination signals from said one or a plurality of digital medical sensors according to the order of the Sort ID built-in in the signal receiving end, and then restoring to a stand-by mode;

wherein the system restores to a stand-by mode, if the identified System ID does not match in Step 1, or if the identified Group ID does not match in Step 2, or if the Reply ID has been identified that a reply is not needed in Step 3; characterized in that the signal receiving end comprises a Group ID identifying function, and an automatic reply function according to the Sort ID.

The System ID, Group ID and Sort ID are all as described above.

The method of identifying the System ID, Group ID and/or Sort ID can adopt an arbitrary conventional hardware, firmware and/or software identification method.

The method of calculating delay time of automatic reply based on the Sort ID and carrying out the delay time and then reply can adopt an arbitrary conventional hardware, firmware and/or software method.

The following embodiments of the present invention all adopt a software/firmware method to solve the above-mentioned problems.

The above-mentioned method is applicable on a wired transmission and a radio transmission, particularly on a radio transmission. When applied on a radio transmission, the above-mentioned monitoring system of the present invention is preferred.

The term "data" used in the present invention include various IDs, check code (C), prefix code (P), data or command (D/C), etc. For example, see Example 1.

In order to further elaborate the present invention, a preferred embodiment together with related flowcharts are described as follows:

EXAMPLE 1

The down stream signal structure of an air interface is shown in the following:

| P | S | SID | C | CID/GID | D/C |
|---|---|-----|---|---------|-----|
| 32 | 16 | 14 | 2 | 16 | n | wherein P represents a prefix code which is a continuous 32-bit code encoded according to a data protocol coding; S is a synchronization code and has two bytes for synchronization of the decoding program. When required, said synchronization code can be sent continuously twice (32 bits in total), provided that the whole system shall adopt the same format. C is a check code and has two bits, wherein, for example, 00 and 11 are reserved codes; 01 represents CID; and 10 is GID. SID (14 bits in total), CID and GID (16 bits in total) are defined as in the above. CID and GID are determined according to C, wherein C being 01 is assigned to represent CID, and C being 10 is assigned to represent GID. D/C is data or command and the number of bits thereof is determined according to the need.

The monitoring method is configured in an EEPROM:

| | NO. of bits | Domain | Comments |
|---|---|---|---|
| SID | 14 | | This system adopts a same system code. |
| C | 2 | 01 → CID<br>10 → GID | 00,11 are reserved. |
| CID/GID | 16 | 0~65535 | CID and GID are independent from each other. |
| Sort ID | 8 | 0~255 | The maximum is the number of patients in said group. |
| Unit delay value | 16 | 65536 | Adopt 256 msec. | wherein SID, C, CID/GID follow the definition of air interface; and the Sort ID adopts 8-bit, i.e. the number of patients in each patient group will not exceed 256. Of course, in order to respond to a particular situation where the number of patients in a patient group exceeds 256, the Sort ID can be larger than 8-bit. However, the signal transmission efficiency will deteriorate if the Sort ID becomes too large.

The following shows a case where the GID and the Sort ID of patients are shown in the following Table 1. The numbers in the table are all 16-carry numbers. The topmost row is the GID; and the bottom row is the total number of patients in said group. The left-most column is the CID of each patient. Other numbers in the table represents the Sort IDs in the GIDs shown on the topmost row of the CID patients shown on the left-most column.

TABLE 1

|      | 0000 | 0001 | 0002 | 0003 | 0004 | ... |
|------|------|------|------|------|------|-----|
| 0000 | 01   | 03   | 01   |      | 1A   | ... |
| 0001 |      |      | 02   |      | 01   | ... |
| 0002 | 02   |      | 05   |      | 2B   | ... |
| 0003 |      | 01   |      | 01   | 3D   | ... |
| 0004 |      |      | 03   |      | 05   | ... |
| 0005 |      | 02   | 06   |      | 41   | ... |
| 0006 | 03   | 04   |      | 3    |      | ... |
| 0007 |      |      | 04   |      | 5F   | ... |
| 0008 | 05   | 05   | 1A   | 02   |      | ... |
| 0009 |      |      |      |      |      | ... |
| 000A |      | 2F   | 0B   |      | 82   | ... |
| 000B | 04   |      |      | 04   | 9C   | ... |
| 000C |      |      |      |      |      | ... |
| 000D |      | 35   |      | 06   | 07   | ... |
| 000E |      |      | 2C   | 05   | 08   | ... |
| 000F | 06   | 05   |      |      |      | ... |
| 0010 | 08   | 26   | 0F   |      | A0   | ... |
| 0011 | 07   |      | 0E   | 07   | 0E   | ... |
| .    | .    | .    | .    | .    | .    | .   |
| .    | .    | .    | .    | .    | .    | .   |
| .    | .    | .    | .    | .    | .    | .   |
| 08AF | 18   |      |      | 08   | A5   |     |
| 08B0 |      | 34   |      |      | A8   |     |
| No. of patients | 18 | 35 | 2C | 08 | A8 |  |

From Table 1: The patient 0000 (hereinafter the CID represents the patient name) belongs to the GID 0000, 0001, 0002, 0004. When an air interface group call is 0000 or 0002, the patient 0000 will reply at a $1^{st}$ time (delay time being 256 ms×0). If the air interface group call is 0001, the patient 0000 will reply at a $3^{rd}$ time (delay time being 256 ms×2). If the air interface group call is 0004, the patient 0000 shall reply at a $26^{th}$ time (26×1+10=26) (delay time being 256 ms×25).

By the same token, if the air interface group call of GID0003 is made, only the 8 patients in said group will receive said signal. Under a situation where a reply is needed, said 8 patients in the group will automatically reply according to the sequence of CID0003→0008→0006→000B→000E→000D→0011→08AF at $1^{st}$, $2^{nd}$, $3^{rd}$, $4^{th}$, $5^{th}$, $6^{th}$, $7^{th}$ and $8^{th}$ time, respectively (i.e. the delay time being 0, 256, 512, 1024, 2048, 4096, 8192, 16384 ms, respectively).

If an air interface single call is CID000A, only said patient can receive said signal. If a reply is needed, the reply will be carried out at a $1^{st}$ time (delay time being 0 ms).

The above-mentioned method of determining a group call is carried out by using a software to read the check code C in the received signal, wherein C=01 represents a single call (CID); while C=10 represents a group call (GID).

The above-mentioned delay time can be completed by using a software loop (FOR . . . NEXT) method. The monitoring system carries out an automatic reply by H/L driving, when the delay time is reached.

Figure 3:
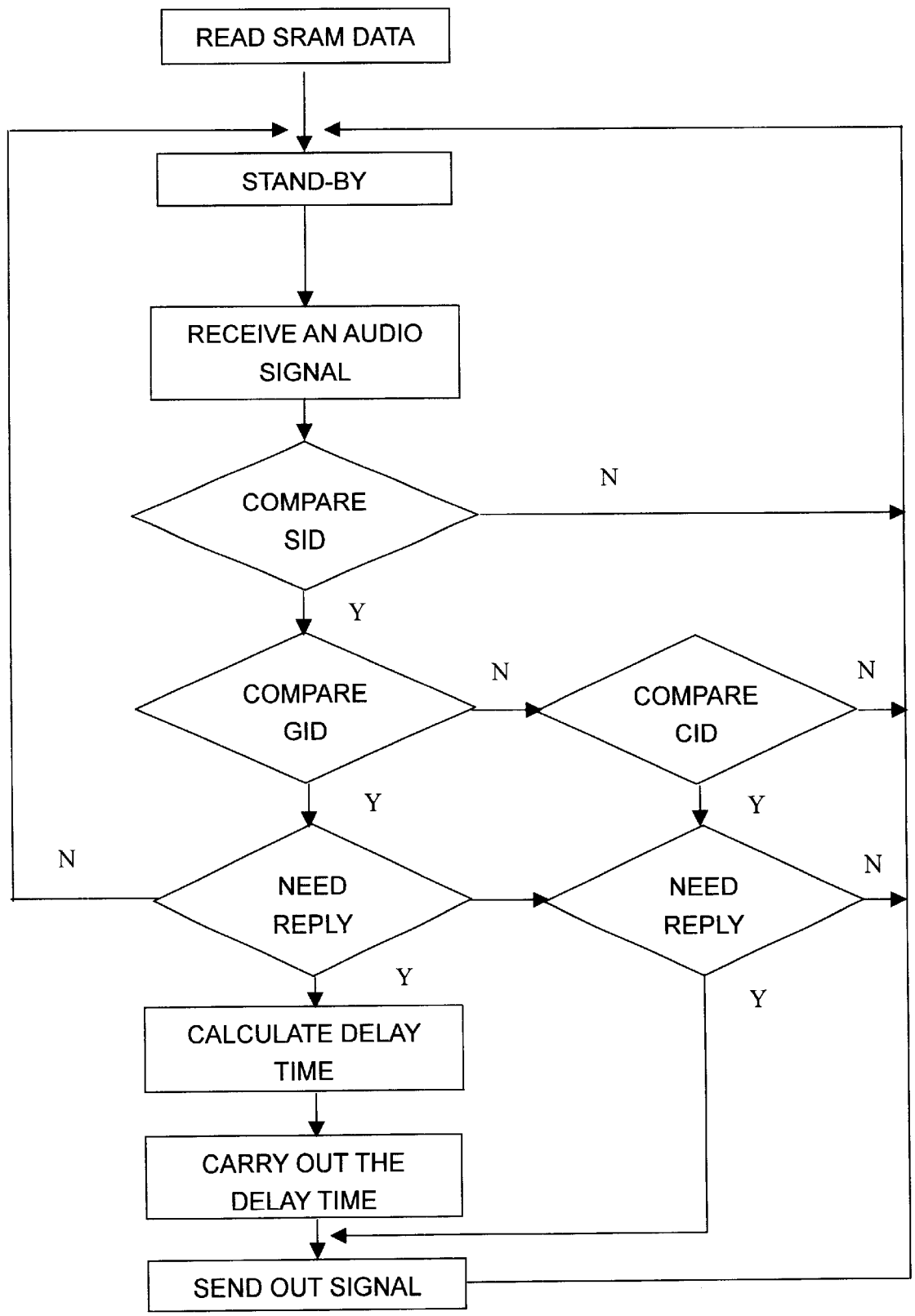
FIG. 3 and FIG. 4 are operation flowcharts of the transmission methods of the radio medical monitoring method according to the present invention.

The above-mentioned method is shown in FIG. 3. The terminal monitoring system first reads the data (including SID, check ID C, CID, Sort ID corresponding to the GID, etc.) in the SRAM; and enters a stand-by state. After receiving a signal, the terminal monitoring system will identify SID, and terminal monitoring system enters stand-by state if the SID does not match. Otherwise, the terminal monitoring system will identify GID. The terminal monitoring system will identify the Reply ID if the GID matches. The terminal monitoring system will calculate the delay time, carry out the delay time, and sent out signals after the delay time has elapsed, if the identification of the Reply ID confirm a reply is needed. The terminal monitoring system will restore the stand-by state, if the identification of the Reply ID confirm a reply is not needed. The terminal monitoring system will restore the stand-by state after sending out the signals.

The terminal monitoring system will identify the CID if the GID does not matches. The terminal monitoring system will restore the stand-by state if the CID does not match. Otherwise, the terminal monitoring system will identify the Reply ID. The terminal monitoring system will sent out signals, if the identification of the Reply ID confirm a reply is needed. The terminal monitoring system will restore the stand-by state, if the identification of the Reply ID confirm a reply is not needed. The terminal monitoring system will restore the stand-by state after sending out the signals.

The delay time DT is calculated according to the following formula:

$$DT = 256 \text{ msec} \times (n_{OD} - 1)$$

wherein $n_{OD}$ represents the value of Sort ID shown in the Table 1. The delay time is carried out with a software means, e.g. using a FOR-NEXT loop.

Figure 4:
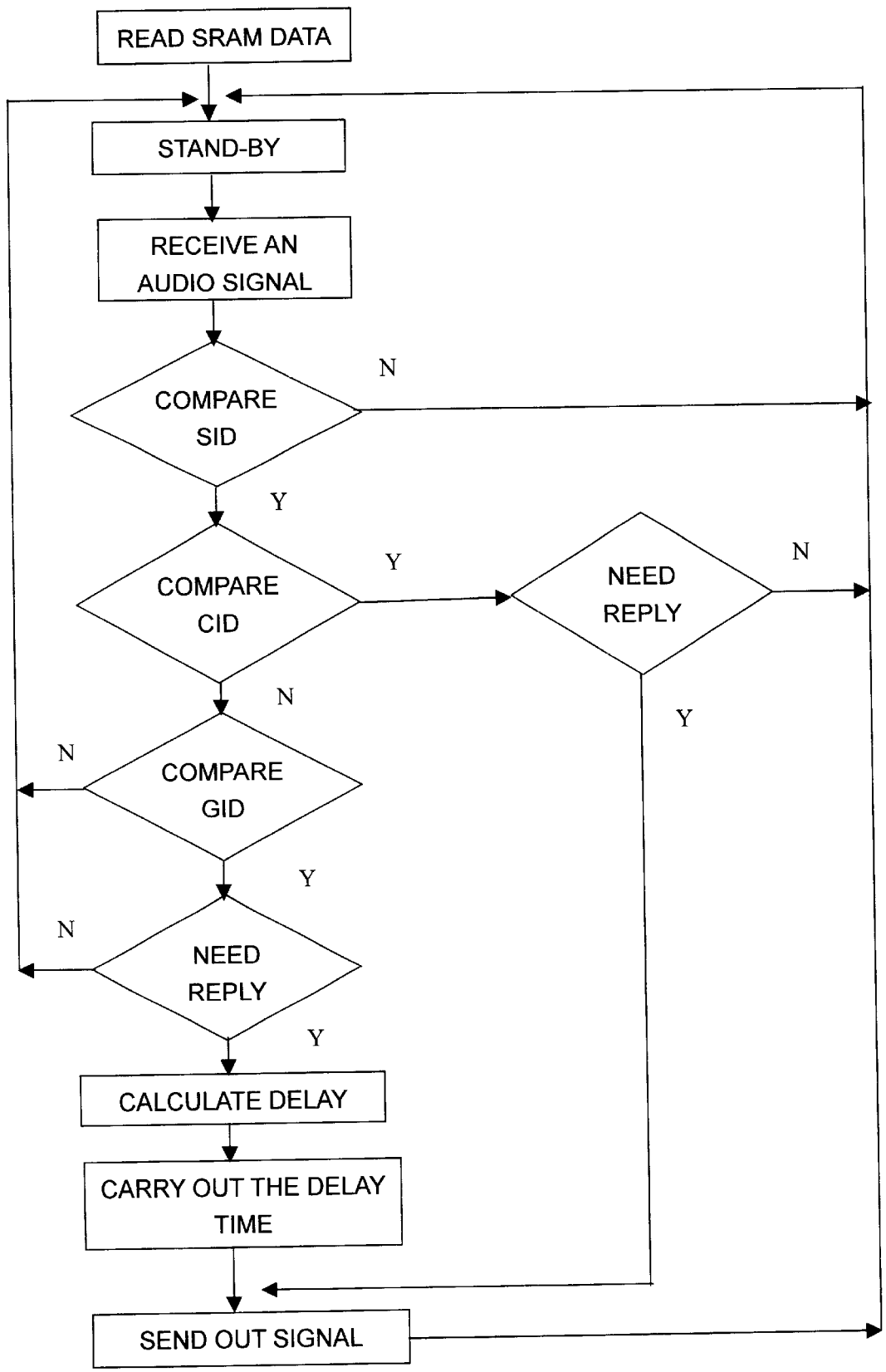

FIG. 4 shows a method similar to the method shown in FIG. 3. The only difference between these two methods is that the method shown in FIG. 3 identifies GID first, then CID; and the method shown in FIG. 4 checks CID first, then GID.

What is claimed is:

1. A radio medical monitoring system comprising:
   a modem;
   a central processing unit (CPU) connected with said modem for digital data transmission therewith;
   a read-only-memory (ROM) connected with said central processing unit;
   a memory connected with said central processing unit;
   one or a plurality of digital medical sensors connected with said central processing unit for transmitting signals from a subject under examination to said central processing unit;
   a radio transceiver connected with said modem for receiving/transmitting radio waves and performing an analog signal transmission with said modem;
   characterized in that said monitoring system has Group ID (GID) and Sort ID functions, and automatically replies according to the order of the Sort ID after identifying the Group ID and confirming that it is necessary to reply.

2. The system as claimed in claim 1, wherein said modem is externally connected with one or more sets of analog devices.

3. The system as claimed in claim 1, wherein said digital medical sensor is a digital human parameter sensor, a medical chemical sensor, a biochemical sensor, or a biosensor.

4. The system as claimed in claim 1, wherein said Group ID and said Sort ID are stored in said ROM and/or said memory.

5. The system as claimed in claim 4, wherein said Group ID and said Sort ID are stored in said memory.

6. The system as claimed in claim 1, wherein said memory is a static random access memory (SRAM).

7. The system as claimed in claim 6, wherein said read-only-memory (ROM) is an electrically erasable programmable read only memory (EEPROM).

8. The system as claimed in claim 1, wherein said read-only-memory (ROM) is an electrically erasable programmable read only memory (EEPROM).

9. A radio medical monitoring method comprising:
 (1) after receiving a signal by a signal receiving end, identifying a System ID in said signal;
 (2) after confirming said System ID, identifying a Group ID in said signal;
 (3) after confirming said Group ID, identifying a Reply ID in said signal;
 (4) after confirming that a reply is needed, automatically and sequentially replying examination signals from digital medical sensors according to the order of the Sort ID built-in in the signal receiving end, and then restoring to a stand-by mode;

wherein a system in which said monitoring method is carried out restores to a stand-by mode, if the identified System ID does not match in Step 1, or if the identified Group ID does not match in Step 2, or if the Reply ID has been identified that a reply is not needed in Step 3; characterized in that the signal receiving end comprises a Group ID identifying function, and an automatic reply function according to the Sort ID.

10. The monitoring method as claimed in claim 9, wherein a delay time DT is generated according to the Sort ID by a software, wherein $DT=\Delta T \times (n-1)$ wherein $\Delta T$ is a unit delay time and n is a Sort ID.

11. The monitoring method as claimed in claim 9, wherein said system in which said monitoring method is carried out is the system defined in claim 1.

* * * * *